United States Patent [19]

Mizukami et al.

[11] Patent Number: 5,686,606
[45] Date of Patent: Nov. 11, 1997

[54] UCF116 COMPOUNDS

[75] Inventors: Tamio Mizukami; Mikito Itoh, both of Machida; Mitsunobu Hara, Sagamihara; Hirofumi Nakano; Yumiko Aotani, both of Machida; Keiko Ochiai, Ebina; Shiro Akinaga, Sunto-gun; Akira Mihara, Machida, all of Japan

[73] Assignee: Kyowa Hakko Kogyo, Co., Ltd., Tokyo, Japan

[21] Appl. No.: 682,514

[22] PCT Filed: Nov. 14, 1995

[86] PCT No.: PCT/JP95/02325

§ 371 Date: Jul. 12, 1996

§ 102(e) Date: Jul. 12, 1996

[87] PCT Pub. No.: WO96/15114

PCT Pub. Date: May 23, 1996

[30] Foreign Application Priority Data

Nov. 15, 1994 [JP] Japan .................. 6-280271

[51] Int. Cl.$^6$ .................. C07D 225/06; A61K 31/415
[52] U.S. Cl. .................. 540/461; 514/183
[58] Field of Search .................. 540/461

[56] References Cited

PUBLICATIONS

Journal of Antibiotics, vol.XLII, No. 3 by Hisayo Nomoto, et al pp. 479–481 (1988).
The Journal of Antibiotics, vol.XXXV, No.11, by Masanori Sugita, et al pp. 1474–1479.
The Journal of Antibiotics, vol. XXXVII, No.6, by Iwao Umezawa, et al pp. 699–698 (1985).
The Journal of Antibiotics, vol. XXXVIII, No. 12, by Shinji Funayama, et al. pp. 1677–1683.
The Journal of Antibiotics, vol. XXXVIII, No.8, pp. 1107–1109 (1985).
The Journal of Antibiotics,vol. XXXV, No.11, by Masanori Sugita, et al. pp. 1460–1473.
Journal of Antibiotics, vol.XLI, No.9, by Shinji Funayama, et al pp. 1223–1231 (1988).
Tetrahedron Letters, vol.32, No.7, pp. 841–842 (1991).
Tetrahedron Letters, vol.32, No.13, pp. 1627–1630 (1991).

*Primary Examiner*—Robert T. Bond
*Attorney, Agent, or Firm*—Antonelli, Terry, Stout & Kraus, LLP.

[57] ABSTRACT

The present invention relates to UCF116 compounds represented by the formula (I):

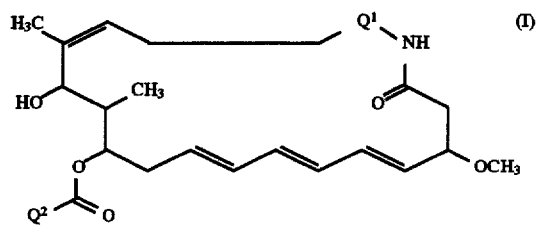

wherein an example of $Q^1$ representation is

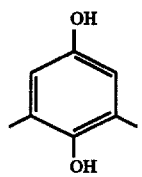

and an example of $Q^2$ representation is

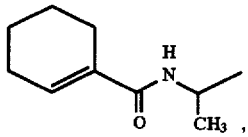

which have antibacterial and antitumor activity and are useful as antibacterial and antitumor agents.

1 Claim, No Drawings

UCF116 COMPOUNDS

This application is a 371 of PCT/JP45/02325 filed Nov. 14, 1995, which claims the priority of Japanese Application 6 280,271, filed 15 Nov. 1994.

TECHNICAL FIELD

The present invention relates to UCF116 compounds which have antibacterial and antitumor activity and are useful as antibacterial and antitumor agents.

BACKGROUND ART

Mycotrienin II having antibacterial and antitumor activity which is represented by the following formula (A) and Mycotrienin I having antibacterial and antitumor activity which is represented by the following formula (B) are known [The Journal of Antibiotics, 35, 1460 (1982), Tetrahedron Letters, 32, 841 (1991)].

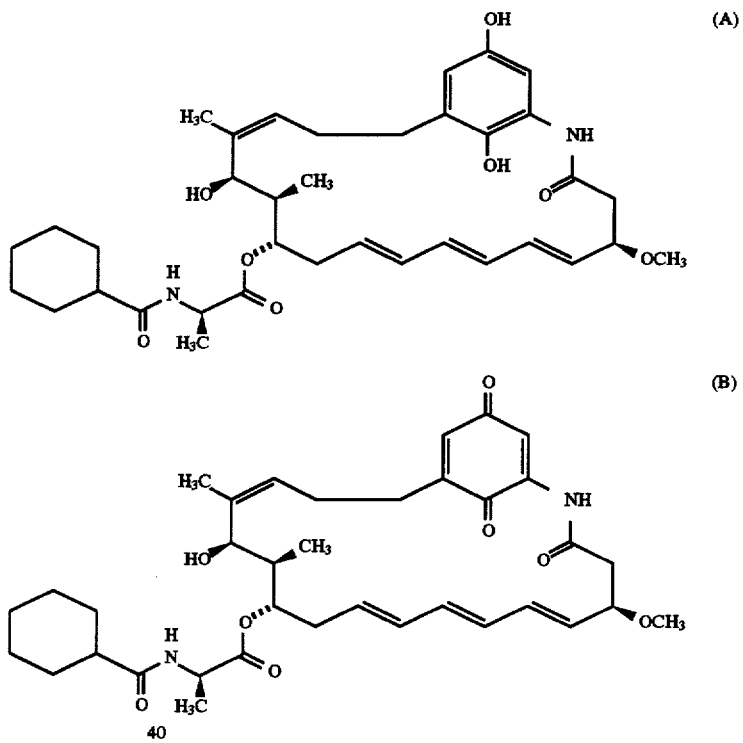

Further, the following compounds are known: Trienomycin A having antibacterial and antitumor activity which is represented by the formula (C):

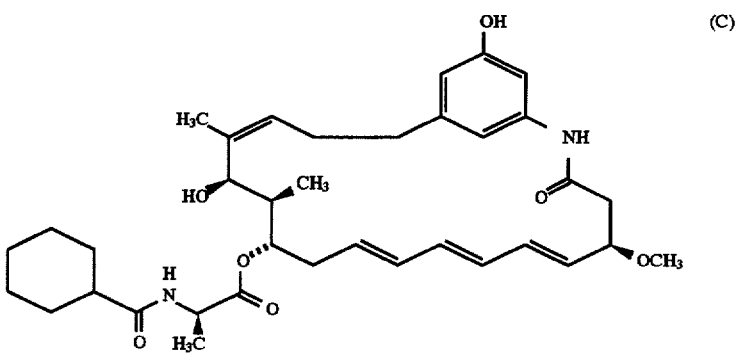

[The Journal of Antibiotics, 38, 699 (1985), The Journal of Antibiotics, 38, 1107 (1985)]; Trienomycin B; Trienomycin C [The Journal of Antibiotics, 38, 1677 (1985)]; Trienomycin D; Trienomycin E [The Journal of Antibiotics, 42, 479 (1989)]; and Trienomycin F which is represented by the formula (D):

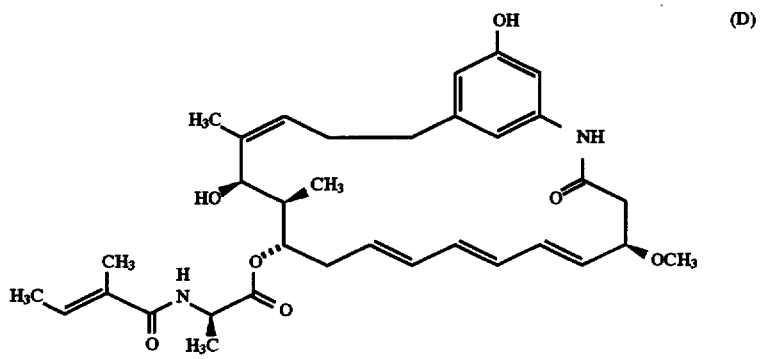

[Tetrahedron Letters, 32, 1627 (1991)].

DISCLOSURE OF THE INVENTION

The present invention provides UCF116 compounds having antibacterial and antitumor activity which are represented by the formula (I):

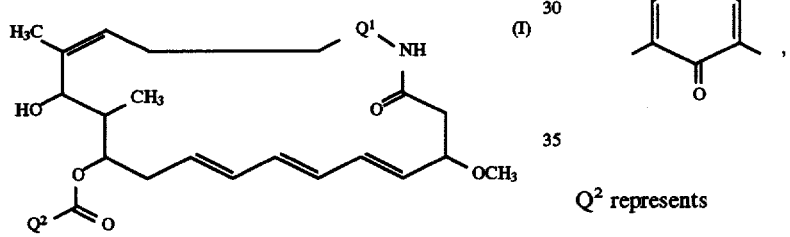

wherein when $Q^1$ is

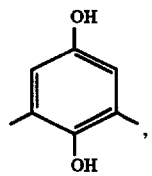

$Q^2$ represents

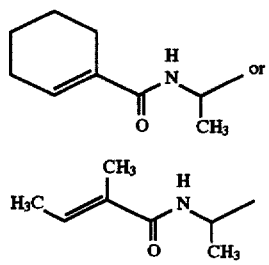

and when $Q^1$ is $Q^2$ represents

UCF116 compounds can be produced by cultivating a microorganism belonging to the genus Streptomyces.

The present invention is described in detail below.

UCF116 compounds include compounds represented by the formulae (1a), (1b) and (1c), respectively. The compound represented by the formula (1a):

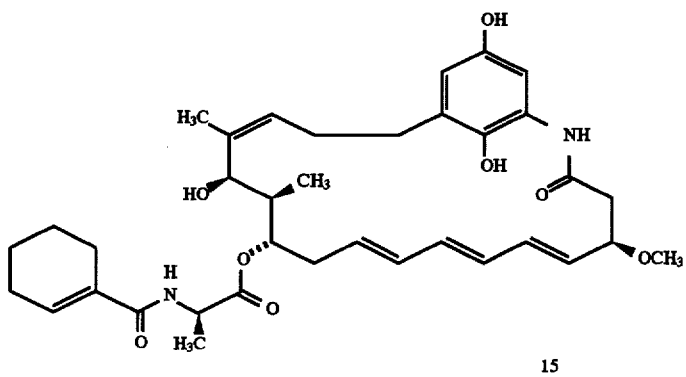

is referred to as UCF116-B, the compound represented by the formula (1b):

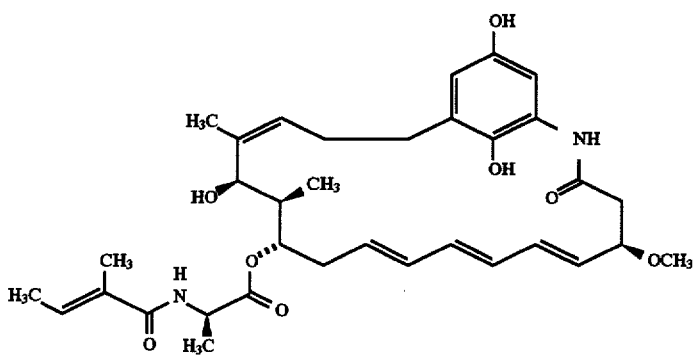

is referred to as UCF116-D, and the compound represented by the formula (1c):

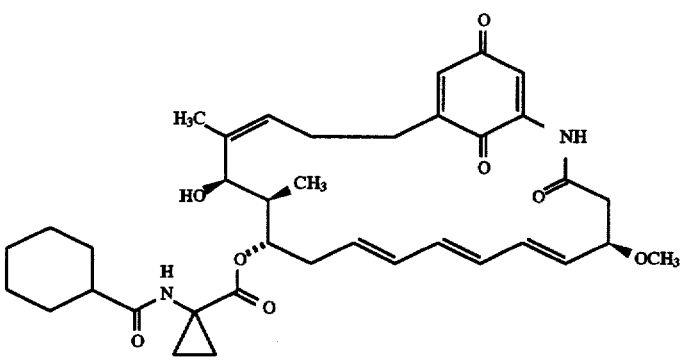

is referred to as UCF116-A3.

The physicochemical properties of UCF116 compounds are shown below.

(i) UCF116-B
Color and form of the substance:
  White powder
Specific rotation:

$[\alpha]_D^{28}$ 32 +327° (c=0.134, $CH_3OH$)

Mass spectrum:
  Positive ion FAB-MS m/z 637.3509 $[M+H]^+$
  (calculated for $C_{36}H_{49}N_2O_8$:637.3489)
Molecular formula:

$C_{36}H_{48}N_2O_8$

UV absorption spectrum:
  $\lambda_{max}$ nm($\epsilon$) ($CH_3OH$): 304(3,300), 280(31,300), 271(40,900), 260(31,600), 206(42,100)
IR absorption spectrum:
  $\nu_{max}$ $cm^{-1}$ (KBr): 3367, 1732, 1653, 1539, 1219, 999
$^1$H-NMR spectrum ($CDCl_3$):
  δ ppm (integration): 8.15(1H), 7.00(1H), 6.69(1H), 6.57 (1H), 6.52(1H), 6.28(1H), 6.24(1H), 6.23(1H), 6.04 (1H), 6.03(1H), 5.65(1H), 5.49(1H), 5.15(1H), 4.93 (1H), 4.71(1H), 4.49(1H), 4.19(1H), 3.35(3H), 2.94 (1H), 2.89(1H), 2.58(1H), 2.52(1H), 2.3(1H), 2.25 (1H), 2.20(2H), 2.2(1H), 2.15(2H), 2.05(1H), 1.87 (1H), 1.73(3H), 1.65(2H), 1.55(2H), 1.47(3H), 0.82 (3H)
C-NMR spectrum ($CDCl_3$):

δ ppm (multiplicity): 173.4(s), 169.6(s), 168.9(s), 149.0 (s), 141.2(s), 138.0(s), 135.8(d), 134.9(d), 134.4(d), 133.8(d), 132.8(s), 132.0(s), 129.5(d), 129.5(d), 129.2 (d), 125.4(s), 124.0(d), 115.8(d), 107.4(d), 79.6(d), 75.8(d), 68.6(d), 56.7(q), 49.0(d), 43.1(d), 39.0(d), 33.7 (t), 31.7(t), 26.5(t), 25.5(t), 24.1(t), 22.0(t), 21.4(t), 20.4(q), 17.8(q), 9.7(q)

Solubility:
Soluble in dimethylsulfoxide (DMSO), chloroform, acetone and ethyl acetate; insoluble in water and hexane.

Color reaction:
Positive to the iodine test

Thin layer chromatography:
Rf value; 0.3
Thin layer; silica gel thin layer (HPTLC plate Art.5715, Merck & Co., Inc.)
Developing solvent; hexane:ethyl acetate:methanol (6:3:1 v/v)
After the development, the spot of UCF116-B can be detected with the iodine reagent.

(ii) UCF116-D
Color and form of the substance:
White powder
Specific rotation:

$[\alpha]_D^{24} = +77.0°$ (c=0.100, CH$_3$OH)

Mass spectrum:
Positive ion FAB-MASS m/s 611.3356 [M+H]$^+$ (calculated for C$_{34}$H$_{47}$O$_8$N$_2$: 611.3333)

Molecular formula:

C$_{34}$H$_{46}$O$_8$N$_2$

UV absorption spectrum:
$\lambda_{max}$ nm(ε) (CH$_3$OH): 302(10,900), 283(4,100), 271(13,300), 260(11,200), 204(21,900)

IR absorption spectrum:
$v_{max}$cm$^{-1}$ (KBr): 3421, 1732, 1624, 1537, 1454, 1213, 1001

$^1$H-NMR spectrum (CDCl$_3$):
δ ppm (integration): 8.38(1H), 7.06(1H), 6.56(1H), 6.53 (1H), 6.49(1H), 6.32(1H), 6.3(1H), 6.2(1H), 6.1(1H), 6.0(1H), 5.64(1H), 5.48(1H), 5.16(1H), 4.93(1H), 4.72 (1H), 4.48(1H), 4.18(1H), 3.34(3H), 2.92(1H), 2.87 (1H), 2.58(1H), 2.52(1H), 2.3(1H), 2.25(1H), 2.2(1H), 2.07(1H), 1.9(1H), 1.82(3H), 1.74(3H), 1.73(3H), 1.48 (3H), 0.82(3H)

$^{13}$C-NMR spectrum (CDCl$_3$):
δ ppm (multiplicity): 173.3(s), 169.7(s), 169.7(s), 49.1(s), 141.1(S), 137.9(s), 135.0(d), 134.4(d), 33.8(d), 132.9 (d), 132.8(s), 130.6(s), 129.6(d), 29.5(d), 129.2(d), 125.4(s), 124.0(d), 115.8(d), 07.5(d), 79.7(d), 75.7(d), 68.5(d), 56.6(q), 49.1(d), 3.0(t), 38.8(d), 33.7(t), 31.7 (t), 26.5(t), 20.5(t), 7.7(q), 14.1(q), 12.2(q), 9.7(q)

Solubility:
Soluble in DMSO, chloroform, acetone and ethyl acetate; insoluble in water and hexane.

Color reaction:
Positive to the iodine test

Thin layer chromatography:
Rf value; 0.17
Thin layer; silica gel thin layer (HPTLC plate Art. 5715, Merck & Co., Inc.)

Developing solvent; hexane:ethyl acetate:methanol ( 6:3:0.5 v/v/v)
After the development, the spot of UCF116-D can be detected with the iodine reagent.

(iii) UCF116-A3
Color and form of the substance:
Yellow powder
Specific rotation:

$[\alpha]_D^{24} = +31.3°$ (c=0.127, CH$_3$OH)

Mass spectrum:
positive ion FAB-MASS m/s 649.3510 [M+H]$^+$ (calculated for C$_{37}$H$_{49}$N$_2$O$_8$: 649.3489)

Molecular formula:

C$_{37}$H$_{48}$N$_2$O$_8$

UV absorption spectrum:
$\lambda_{max}$ nm (ε) (CH$_3$OH): 281(26,200), 270(33,400), 262 (26,800), 227(21,500), 203(25,900)

IR absorption spectrum:
$v_{max}$cm$^{-1}$ (KBr): 3440, 2927, 2854, 1716, 1653, 1506, 1180

$^1$H-NMR spectrum (CDCl$_3$):
ε ppm (integration): 8.13(1H), 7.47(1H), 6.48(1H), 6.11 (1H), 6.1(1H), 6.1(1H), 6.1(1H), 6.0(1H), 5.58(1H), 5.50(1H), 5.18(1H), 4.86(1H), 4.48(1H), 4.03(1H), 3.37(3H), 2.84(1H), 2.6(1H), 2.5(1H), 2.4(1H), 2.3 (1H), 2.3(1H), 2.1(1H), 2.0(2H), 1.85(3H), 1.80(3H), 1.75(2H), 1.7(1H), 1.5(2H), 1.35(3H), 1.25(2H), 1.12 (2H), 0.89(3H)

$^{13}$C-NMR spectrum (CDCl$_3$):
δ ppm (multiplicity): 188.3(s), 182.6(s), 177.5(s), 172.4 (s), 169.5(s), 145.5(s), 139.8(s), 138.0(s), 134.0(d), 133.9(d), 133.3(d), 133.1(d), 131.2(d), 129.8(d), 129.4 (d), 122.7(d), 114.6(d), 79.1(d), 75.9(d), 68.0(d), 56.8 (q), 45.2(d), 44.9(t), 40.3(d), 33.7(s), 33.2(t), 29.8(t), 29.7(t), 29.6(t), 29.3(t), 25.70(t), 25.67(t), 25.65(t), 20.7(q), 18.2(t), 17.8 (t), 9.7 (q)

Solubility:
Soluble in DMSO, chloroform, acetone and ethyl acetate; insoluble in water and hexane.

Color reaction:
Positive to the iodine test

Thin layer chromatography:
Rf value; 0.22
Thin layer; silica gel thin layer (HPTLC plate Art.5715, Merck & Co., Inc.)
Developing solvent; hexane:ethyl acetate:methanol (6:3:1 v/v/v)
After the development, the spot of UCF116-A3 can be detected with the iodine reagent.

The above data were obtained by using the following instruments.

Mass spectrum: JEOL LTD., JMS-HX/HX110A Mass spectrometer

UV absorption spectrum: Shimadzu Corporation, UV-2200 Spectrophotometer

IR absorption spectrum: JEOL LTD., JIR-RFX3001 Infrared spectrophotometer NMR spectrum: JEOL LTD., JNM-A400 Nuclear magnetic resonance Bruker, AM500 Nuclear magnetic resonance Optical rotation: Nippon Bunko Kogyo Co., Ltd., DIP-370 Digital polarimeter The biological activities of UCF116 compounds are described below by Test Examples.

TEST EXAMPLE 1

Antibacterial Activity Against Various Bacteria

The minimum inhibitory concentration (MIC) of UCF116 compounds against the growth of various bacteria is shown in Table 1.

The antibacterial activity was determined by the agar dilution method using a medium (pH 7) which comprises 3 g/l Bacto-tryptone (Difco Laboratories), 3 g/l meat extract, 1 g/f yeast extract, 1 g/l glucose and 16 g/l agar.

TABLE 1

| Bacteria tested | MIC (μg/ml) | | |
|---|---|---|---|
| | UCF116-B | UCF116-D | UCF116-A3 |
| Staphylococcus aureus ATCC 6538P | 41.7 | 83.3 | 41.7 |
| Candida albicans ATCC 10231 | 20.8 | 83.3 | 41.7 |
| Enterococcus faecium ATCC 10541 | 41.7 | 83.3 | 83.3 |

TEST EXAMPLE 2

Growth inhibition Against BALB 3T3/H-ras Cells

A BALB 3T3/H-ras cell suspension ($3.0 \times 10^4$ cells/ml) prepared by suspending BALB 3T3/H-ras cells (ATCC HTB22) in a medium comprising MEM medium (Nissui Pharmaceutical Co., Ltd.) and 10% fetal calf serum (hereinafter referred to as Medium A) was put into wells of a 96-well microtiter plate in an amount of 0.1 ml per well. After the cells in the plate were cultivated at 37° C. for 20 hours in a $CO_2$-incubator, a test compound appropriately diluted with Medium A was added to the wells in an amount of 0.1 ml per well. The cells were further cultivated at 37° C. for 72 hours in the $CO_2$-incubator. After the cultivation supernatant was removed, the residue was washed once with physiological saline and then treated with 0.1 ml of methanol for 10 minutes to fix the cells. The cells were stained with 0.1 ml of Giemsa's staining solution [Giemsa's staining solution, Merck Art 9204 (Merck & Co., Inc.): physiological saline=1:10] for 5 minutes. After the staining solution was removed, the residue was washed once with 0.2 ml of water. Then, the dye was extracted with 0.2 ml of 0.1 N hydrochloric acid and the absorbance was measured at 620 nm with a microplate reader.

The concentration of the test compound at which the growth of the cells is inhibited by 50% ($IC_{50}$) was calculated by comparing the absorbance of untreated cells with those of the cells treated with the test compound at known concentrations.

The result is shown in Table 2.

TABLE 2

| Compound | $IC_{50}$ (μM) |
|---|---|
| UCF116-B | 0.39 |
| UCF116-D | 0.66 |

TEST EXAMPLE 3

Growth Inhibition Against HR-3Y1 Cells

An HR-3Y1 cell suspension ($3.0 \times 10^4$ cells/ml) prepared by suspending HR-3Y1 cells in a medium comprising MEM medium (Nissui Pharmaceutical Co., Ltd.) and 10% fetal calf serum (hereinafter referred to as Medium A) was put into wells of a 96-well microtiter plate in an amount of 0.1 ml per well. After the cells in the plate were cultivated at 37° C. for 20 hours in a $CO_2$-incubator, a test compound appropriately diluted with Medium A was added to the wells in an amount of 0.1 ml per well. The cells were further cultivated at 37° C. for 72 hours in the $CO_2$-incubator. After the cultivation supernatant was removed, the residue was washed once with physiological saline and then treated with 0.1 ml of methanol for 10 minutes to fix the cells. The cells were stained with 0.1 ml of Giemsa's staining solution [Giemsa's staining solution, Merck Art 9204 (Merck & Co., Inc.): physiological saline=1:10] for 5 minutes. After the staining solution was removed, the residue was washed once with 0.2 ml of water. Then, the dye was extracted with 0.2 ml of 0.1 N hydrochloric acid and the absorbance was measured at 620 nm with a microplate reader.

The concentration of the test compound at which the growth of the cells is inhibited by 50% ($IC_{50}$) was calculated by comparing the absorbance of untreated cells with those of the cells treated with the test compound at known concentrations.

The result is shown in Table 3.

TABLE 3

| Compound | $IC_{50}$ (μM) |
|---|---|
| UCF116-B | 0.35 |
| UCF116-A3 | 0.95 |

TEST EXAMPLE 4

Antitumor Activity Against Isogenic Tumor System in K-BALB Mice

The antitumor activity against an isogenic tumor system in K-BALB mice was measured according to the method described in Proc. Natl. Acad. Sci., 90, 2281 (1993). That is, an isogenic tumor in K-BALB mice was resected from a donor mouse, and a $2 \times 2 \times 2$ mm (8 mm$^3$) tumor piece was subcutaneously transplanted into a BALB/c mouse at the ventral side using a trocar. After the graft survival was confirmed on the 7th day after the transplantation, a test compound was intraperitoneally administered for 5 consecutive days from the same day. The longer diameter and the shorter diameter of the tumor were measured with slide calipers, and the tumor volume was calculated according to the formula: (longer diameter)×(shorter diameter)$^2$/2 [Cancer Chemother. Rep., Part III, 3, 1 (1972)]. The antitumor effect was evaluated in terms of T/C, the ratio of the tumor volume of a test compound-treated group (T) to that of an untreated group (C).

The result is shown in Table 4.

TABLE 4

| Compound | Dose (mg/kg) | T/C |
|---|---|---|
| UCF116-B | 10.0 | 0.25 |

The process for producing UCF116 compounds is described below.

UCF116 compounds can be obtained by cultivating in a medium a microorganism belonging to the genus Streptomyces and having the ability to produce UCF116 compounds, allowing UCF116 compounds to accumulate in the culture, and recovering UCF116 compounds from the culture.

As the UCF116-compound-producing strains of the present invention, any strains which belong to the genus Streptomyces and have the ability to produce UCF116 compounds can be used. In addition, any mutants of such strains which are obtained by various artificial mutation methods such as UV irradiation, X ray irradiation and treatment with mutagens or by spontaneous mutation may also be used in the present invention, insofar as they have the ability to produce UCF116 compounds. A typical example of a suitable strain is Streptomyces sp. UCF116 strain.

The mycological properties of Streptomyces sp. UCF116 strain are described below.

The properties were studied according to the method recommended by the International Streptomyces Project (ISP) for the characterization of the Streptomyces species [E. B. Shirling and D. Gottlieb: Int. J. Syst. Bacteriol., 16, 313–340 (1966)].

The stereoisomer of diaminopimelic acid in the whole-cell hydrolyzate was identified by the method of B. Becker et al. [Appl. Microbiol., 12, 421–423 (1964)].

The morphological investigations were made under an optical microscope. For spore surface morphology, in particular, a scanning electron microscope was used.

The color names were given according to the Color Harmony Manual (Container Corporation of America, 4th edition, 1958).

1. Morphological characteristics
   1) Hyphae
   Formation of aerial hyphae: Observed
   Fragmentation and motility of aerial hyphae: Not observed
   Fragmentation and motility of substrate hyphae: Not observed
   2) Spores
   Formation and location of spores: Formed on the aerial hyphae
   Formation and location of sporangia: Not observed
   Number of spores in chain formed at the end of the sporophore; 10 or more
   Form of spore chains; Flexuous or spiral chains
   Characteristics of spores:
     Surface; Smooth
     Form and size; Bacilliform, ca. 0.5 ~0.7 μm×0.8 ~1.0
   Motility of spores and existence of flagella; Not observed
   3) Others
   Chlamydospores; Not observed
   Synnemata; Not observed
   Pseudosporangia; Not observed
   Branching mode of hyphae; Simple branching 2. Cultural characteristics The strain UCF116 shows moderate or good growth on synthetic media and natural media which are generally used. The color of the substrate hyphae is yellow to brown. Formation of soluble brown pigment was observed on some of the culture.

The cultural characteristics such as growth and color of UCF116 strain on various agar media observed after cultivating at 28° C. for 14 days are shown below.

1) Sucrose—nitrate agar medium
Degree of growth; Good
Color of substrate hyphae; Covert tan (2 ge)
Formation and color of aerial hyphae; None
Soluble pigment; None 2) Glucose—asparagine agar medium
Degree of growth; Good
Color of substrate hyphae; Bamboo (2 gc)—light gold (2 ic)
Formation and color of aerial hyphae; Abundant, white (a)—gray (e)
Soluble pigment; Formed (yellow)

3) Glycerol—asparagine agar medium
Degree of growth; Good
Color of substrate hyphae; Bamboo (2 gc)—mustard tan (2 lg)
Formation and color of aerial hyphae; Abundant, white (a)
Soluble pigment; Formed (pale yellow)

4) Starch—inorganic salts agar medium
Degree of growth; Good
Color of substrate hyphae; Light ivory (2 ca)—light mustard tan (2 ie)
Formation and color of aerial hyphae; Abundant, white (a)—dark brown (3 nl)
Soluble pigment; None 5) Tyrosine agar medium
Degree of growth; Good
Color of substrate hyphae; Light beige (3 ec)—clove brown (3 ni)
Formation and color of aerial hyphae; Abundant, white (a)
Soluble pigment; Formed (reddish brown)

6) Nutrient agar medium
Degree of growth; Moderate
Color of substrate hyphae; Maize (2 ga)
Formation and color of aerial hyphae; Abundant, white (a)
Soluble pigment; None 7) Yeast—malt agar medium
Degree of growth; Good
Color of substrate hyphae; Camel (3 ie)—light brown (3 lg)
Formation and color of aerial hyphae; Abundant, white (a)—lamp black (p)
Soluble pigment; None 8) Oatmeal agar medium
Degree of growth; Good
Color of substrate hyphae; Pearl pink (3 ca)—dark brown (3 nl)
Formation and color of aerial hyphae; Abundant, white (a)—lamp black (p)
Soluble pigment; None 3. Physiological characteristics The physiological characteristics of UCF116 strain are shown below. Growth temperature range was determined after 10 days of cultivating and the other observations were made after 2 to 3 weeks of cultivating at 28° C.

1) Growth temperature range; 6.0°–41.0° C.
2) Liquefaction of gelatin; Positive
3) Hydrolysis of starch; Positive
4) Coagulation and peptonization of skim milk powder; Peptonized
5) Production of melanin-like pigment
   (i) Peptone—yeast—iron agar medium; Negative
   (ii) Tyrosine agar medium; Positive 6) Assimilability of carbon sources (As the basis medium, Pridham Gottlieb agar medium was used.)
+: Assimilable—: Nonassimilable
L-Arabinose; +
D-Xylose; +
D-Glucose; +
Sucrose; +
Raffinose; +
D-Fructose; +
L-Rhamnose; +
Inositol; +
D-Mannitol; +

4. Chemotaxonomic characteristics

Configuration of diaminopimelic acid in whole-cell hydrolyzate; LL-form

The strain is classified in the Type I cell wall group (LL-diaminopimelic acid, glycine) from the above chemotaxonomic characteristics according to the classification of actinomycetes by M. P. Lechevalier and H. A. Lechevalier [Int. J. Syst. Bacteriol., 20, 435–443 (1970)]. On the basis of this characteristic and the morphological characteristics, e.g. formation of spore chains on aerial hyphae, it is reasonable to regard the strain as belonging to the genus Streptomyces.

The present strain was named Streptomyces sp. UCF116 based on the above results. The strain was deposited with the National Institute of Bioscience and Human-Technology, Agency of Industrial Science and Technology on Oct. 25, 1994 with accession number FERM BP-4845 under the Budapest Treaty.

For the cultivating of the UCF116-compound-producing strains used in the present invention, conventional methods for cultivating actinomycetes are generally employed. As the medium, either a synthetic medium or a natural medium may be used insofar as it appropriately contains carbon sources, nitrogen sources and inorganic substances which can be assimilated by the strains employed and the growth—and production-promoting substances required.

As the carbon sources, glucose, starch, dextrin, mannose, fructose, sucrose, lactose, xylose, arabinose, mannitol, molasses, etc. can be used alone or in combination. In addition, hydrocarbons, alcohols, organic acids, etc. may also be used according to the assimilability of the microorganism employed.

As the nitrogen sources, ammonium chloride, ammonium nitrate, ammonium sulfate, sodium nitrate, urea, peptone, meat extract, yeast extract, dry yeast, corn steep liquor, soybean powder, casamino acid, etc. can be used alone or in combination.

If necessary, inorganic salts such as sodium chloride, potassium chloride, magnesium sulfate, calcium carbonate, potassium dihydrogen phosphate, ferrous sulfate, calcium chloride, manganese sulfate, zinc sulfate, and copper sulfate may be added. In addition, trace ingredients that promote the growth of the strain employed and the production of UCF116 compounds may also be added to the medium.

As the method of cultivating, liquid culture, especially submerged stirring culture, is preferably employed. Cultivating is carried out at 16 to 37° C., preferably 25 to 32° C., and at pH 4 to 10, preferably 6 to 8. In general, cultivating is completed in 1 to 7 days, and UCF116 compounds are produced and accumulated in the culture and the microbial cells.

In order to adjust the pH of the medium, aqueous ammonia, ammonium carbonate solution, etc. are used. When the amount of the product in the culture reaches the maximum, the cultivating is discontinued.

For the isolation and purification of UCF116 compounds from the culture, an ordinary method for isolating a microbial metabolite from the culture can be utilized.

For example, the culture is separated into culture filtrate and microbial cells by filtration. Extraction of UCF116 compounds with chloroform, acetone, or the like from the microbial cells is carried out. Then, the extract is mixed with the culture filtrate, and the resulting mixture is passed through a column of polystyrene adsorbent such as Diaion HP20 (Mitsubishi Kasei Corporation) to adsorb the active substance, followed by elution with ethyl acetate, acetone, or the like. The eluate is concentrated, and the concentrate is subjected to silica gel column chromatography, high performance liquid chromatography, and the like to give UCF116 compounds. During the cultivation and purification steps, UCF116 compounds can be traced by silica gel thin layer chromatography, followed by detection with iodine reagent.

Examples of the present invention are shown below.

BEST MODE FOR CARRYING OUT THE INVENTION

EXAMPLE 1

Streptomyces sp. UCF116 strain (FERM BP-4845) was used as the seed strain.

The strain was inoculated into 300 ml of a seed medium having the following composition in a 2-l Erlenmeyer flask, and cultivated with shaking (rotation: 200 rpm) at 30° C. for 48 hours.

Composition of the seed medium: 30 g/l sucrose, 20 g/l soluble starch, 30 g/l corn steep liquor, 5 g/l dry yeast, and 2 g/l calcium carbonate (pH 7.0 before sterilization)

The resulting seed culture was transferred into 18 l of a fermentation medium having the following composition in a 30-l jar fermentor in an amount of 5% (by volume) of the fermentation medium and cultivating was carried out at 28° C. with stirring and aeration (rotation: 300 rpm, aeration: 18 l/min.).

composition of the fermentation medium: 25 g/l glycerol, 25 g/l glucose, 30 g/l corn steep liquor, 10 g/l dry yeast, 0.5 g/l $KH_2PO_4$, 0.5 g/l $MgSO_4.7H_2O$, and 5 g/l calcium carbonate (pH 7.0 before sterilization, adjusted with NaOH)

Cultivation was carried out for 70 hours without controlling the pH of the medium. The resulting fermentation culture was separated into culture filtrate and microbial cells by filtration. Extraction of UCF116 compounds with acetone from the microbial cells was carried out, and the extract was concentrated. The concentrate was applied to a column of silica gel (Lichroprep Si60, Merck & Co., Inc.), followed by development with chloroform-methanol (150:1 v/v). The eluted active fraction was concentrated, and the concentrate was applied to a column of silica gel (Lichroprep Si60, Merck & Co., Inc.), followed by development with hexane-ethyl acetate-methanol (6:3:1 v/v/v) and fractionation. The eluted active fraction was concentrated, and the concentrate was subjected to high performance liquid chromatography (HPLC) under the following conditions. Development was carried out with acetonitrile-water (1:1 v/v), and the fraction containing UCF116-B (retention time: 45–47 minutes) and the fraction containing UCF116-D (retention time: 34–36 minutes) were respectively obtained. Each fraction was concentrated and water was added to the residue, followed by extraction with ethyl acetate. The extract was dehydrated over anhydrous sodium sulfate, and concentrated to give 7 mg of UCF116-B as white powder and 12 mg of UCF116-D as white powder, respectively.

HPLC conditions

Column: ODS 120A S-5 (SH363-5) (YMC)

Eluent: 50% acetonitrile
Flow rate: 10 ml/min
Detection: 270 nm
Retention time: UCF116-B; 47 minutes
UCF116-D; 35 minutes

EXAMPLE 2

Streptomyces sp. UCF116 strain (FERM BP-4845) was cultivated in the same manner as in Example 1 to obtain fermentation culture of the strain.

The resulting fermentation culture was separated into culture filtrate and microbial cells by filtration. Extraction of UCF116 compounds with acetone the microbial cells is carried out, and the extract was concentrated. The concentrate was applied to a column of silica gel (Lichroprep Si60, Merck & Co., Inc.), followed by development with hexane-ethyl acetate-methanol (6:3:1 v/v/v) and fractionation. The eluted active fraction was concentrated, and the concentrate was subjected to high performance liquid chromatography (HPLC) under the following conditions. Development was carried out with acetonitrile-water (5.5:4.5 v/v), and the fraction containing UCF116-A3 (retention time: 47–48 minutes) was obtained. The fraction was concentrated and water was added to the residue, followed by extraction with ethyl acetate. The extract was dehydrated over anhydrous sodium sulfate, and concentrated to give 14 mg of UCF116-A3 as yellow powder.

HPLC conditions

Column: INERTSIL PREP-ODS (GL SCIENCES)
    Eluent: 55% acetonitrile
    Flow rate: 10 ml/min
    Detection: 270 nm
    Retention time: UCF116-A3; 47 minutes Industrial Applicability According to the present invention, UCF116 compounds which have antibacterial and antitumor activity can be provided.

We claim:

1. UCF116 compounds which are represented by the formula ( I ):

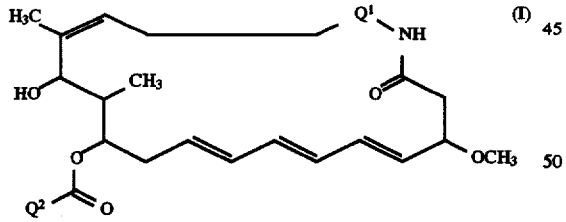

wherein when $Q^1$ is

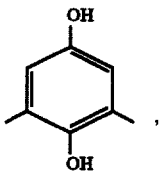

$Q^2$ represents

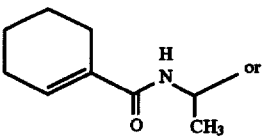

or

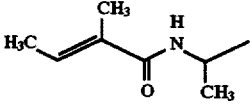

and when $Q^1$ is

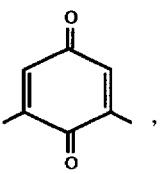

$Q^2$ represents

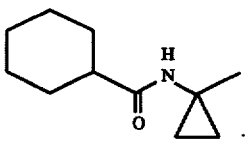

* * * * *